(12) United States Patent
Heuser

(10) Patent No.: US 7,374,567 B2
(45) Date of Patent: May 20, 2008

(54) CATHETER SYSTEM FOR CONNECTING ADJACENT BLOOD VESSELS

(76) Inventor: Richard R. Heuser, 500 W. Thomas Rd., Suite 900, Phoenix, AZ (US) 85013

( * ) Notice: Subject to any disclaimer, the term of this patent is extended or adjusted under 35 U.S.C. 154(b) by 0 days.

(21) Appl. No.: 11/340,324

(22) Filed: Jan. 25, 2006

(65) Prior Publication Data
US 2007/0173878 A1   Jul. 26, 2007

(51) Int. Cl.
*A61B 17/34* (2006.01)
*A61B 17/08* (2006.01)

(52) U.S. Cl. ...................... 606/185; 606/153
(58) Field of Classification Search ............... 606/153, 606/167, 170, 181, 184, 185, 219–220, 213–215; 623/1.11; 227/175.1, 182.1
See application file for complete search history.

(56) References Cited

U.S. PATENT DOCUMENTS

| | | |
|---|---|---|
| 2,729,211 A | 1/1956 | Peter |
| 3,751,305 A | 8/1973 | Huebscher |
| 3,788,318 A | 1/1974 | Kim et al. |
| 3,828,770 A | 8/1974 | Kuris et al. |
| 3,828,782 A | 8/1974 | Polin |
| 4,241,289 A | 12/1980 | Bowling |
| 4,430,081 A | 2/1984 | Timmermans |
| 4,445,892 A | 5/1984 | Hussein et al. |
| 4,590,669 A | 5/1986 | Imamura |
| 4,637,814 A | 1/1987 | Leiboff |
| 4,650,466 A | 3/1987 | Luther |
| 4,682,981 A | 7/1987 | Suzuki et al. |

(Continued)

FOREIGN PATENT DOCUMENTS

EP   0696447   2/1996

(Continued)

OTHER PUBLICATIONS

JAMA: *Effects of an Arteriovenous Fistula on the Devascularized Limb*. Feb. 22, 1965.

(Continued)

*Primary Examiner*—Michael J. Hayes
*Assistant Examiner*—Christina Gettman
(74) *Attorney, Agent, or Firm*—Kolisch Hartwell, P.C.

(57) ABSTRACT

A catheter system is provided for creating a fistula between blood vessels, using a first catheter with a piercing tool adjacent its distal end, and a second catheter with a receptor adjacent its distal end. The receptor includes an opening and a channel providing a guide surface for receiving the piercing tool. The receptor and piercing tool include one or more magnets to draw the piercing tool into the channel of the receptor. The piercing tool and the receptor are provided with a complementary configuration, such as a mating conical shapes. A third catheter may be provided with a double balloon for use in sealing off the fistula site. The piercing tool may be provided on a metal guidewire that includes a lumen with a distal opening. The piercing tool may include a base and a needle coupled to the base at a nominal angle of at least about 20-degrees. The piercing tool may be selectively moved between an extended position wherein the needle is positioned outside the guidewire at the nominal angle and a retracted position wherein the needle is positioned substantially within the guidewire.

21 Claims, 4 Drawing Sheets

U.S. PATENT DOCUMENTS

| | | |
|---|---|---|
| 4,706,671 A | 11/1987 | Weinrib |
| 4,744,364 A | 5/1988 | Kensey |
| 4,771,777 A | 9/1988 | Horzewski et al. |
| 4,772,258 A | 9/1988 | Marangoni et al. |
| 4,796,640 A | 1/1989 | Webler |
| 4,832,688 A | 5/1989 | Sagae et al. |
| 4,862,891 A | 9/1989 | Smith |
| 4,883,460 A | 11/1989 | Zanetti |
| 4,895,564 A | 1/1990 | Farrell |
| 4,911,163 A | 3/1990 | Fina |
| 4,950,257 A | 8/1990 | Hibbs et al. |
| 4,994,071 A | 2/1991 | MacGregor |
| 5,078,684 A | 1/1992 | Yasuda |
| 5,092,846 A | 3/1992 | Nishijima et al. |
| 5,112,310 A | 5/1992 | Grobe |
| 5,147,336 A | 9/1992 | Wendell et al. |
| 5,163,906 A | 11/1992 | Ahmadi |
| 5,176,144 A | 1/1993 | Yoshikoshi et al. |
| 5,199,939 A | 4/1993 | Dake et al. |
| 5,207,228 A | 5/1993 | Roelandt et al. |
| 5,213,417 A | 5/1993 | Yamada et al. |
| 5,217,019 A | 6/1993 | Hughes |
| 5,217,484 A | 6/1993 | Marks |
| 5,234,437 A | 8/1993 | Sepetka |
| 5,242,410 A | 9/1993 | Melker |
| 5,256,141 A | 10/1993 | Gencheff et al. |
| 5,256,158 A | 10/1993 | Tolkoff et al. |
| 5,257,979 A | 11/1993 | Jagpal |
| 5,261,878 A | 11/1993 | Galindo |
| 5,275,488 A | 1/1994 | Stelts |
| 5,281,793 A | 1/1994 | Gavin et al. |
| 5,290,310 A | 3/1994 | Makower et al. |
| 5,320,617 A | 6/1994 | Leach |
| 5,330,486 A * | 7/1994 | Wilk ..................... 606/139 |
| 5,354,271 A | 10/1994 | Voda |
| 5,356,486 A | 10/1994 | Sugarman et al. |
| 5,364,392 A | 11/1994 | Warner et al. |
| 5,370,459 A | 12/1994 | Culbertson et al. |
| 5,399,088 A | 3/1995 | Mechley |
| 5,415,635 A | 5/1995 | Bagaoisan et al. |
| 5,437,292 A | 8/1995 | Kipshidze et al. |
| 5,439,446 A | 8/1995 | Barry |
| 5,443,478 A | 8/1995 | Purdy |
| 5,445,646 A | 8/1995 | Euteneuer et al. |
| 5,458,573 A | 10/1995 | Summers |
| 5,462,359 A | 10/1995 | Reichl et al. |
| 5,462,529 A | 10/1995 | Simpson et al. |
| 5,512,291 A | 4/1996 | Li |
| 5,545,193 A | 8/1996 | Fleischman et al. |
| 5,545,209 A | 8/1996 | Roberts et al. |
| 5,549,626 A | 8/1996 | Miller et al. |
| 5,578,008 A | 11/1996 | Hara |
| 5,591,137 A | 1/1997 | Stevens |
| 5,591,206 A * | 1/1997 | Moufarrege ............... 606/215 |
| 5,599,325 A | 2/1997 | Ju et al. |
| 5,620,457 A | 4/1997 | Pinchasik et al. |
| 5,628,786 A | 5/1997 | Banas et al. |
| 5,632,760 A | 5/1997 | Sheiban et al. |
| 5,632,762 A | 5/1997 | Myler |
| 5,645,560 A | 7/1997 | Crocker et al. |
| 5,660,473 A | 8/1997 | Noma et al. |
| 5,665,107 A | 9/1997 | Hammerslag |
| 5,667,523 A | 9/1997 | Bynon et al. |
| 5,674,241 A | 10/1997 | Bley et al. |
| 5,681,295 A | 10/1997 | Gyure et al. |
| 5,683,453 A | 11/1997 | Palmaz |
| 5,688,266 A | 11/1997 | Edwards et al. |
| 5,695,498 A | 12/1997 | Tower |
| 5,707,359 A | 1/1998 | Bufalini |
| 5,725,524 A | 3/1998 | Mulier et al. |
| 5,725,572 A | 3/1998 | Lam et al. |
| 5,728,068 A | 3/1998 | Leone et al. |
| 5,733,044 A | 3/1998 | Rose et al. |
| 5,733,267 A | 3/1998 | Del Toro |
| 5,735,892 A | 4/1998 | Myers et al. |
| 5,743,900 A | 4/1998 | Hara |
| 5,749,880 A | 5/1998 | Banas et al. |
| 5,762,630 A | 6/1998 | Bley et al. |
| 5,769,077 A | 6/1998 | Lindgren |
| 5,792,070 A | 8/1998 | Kauphusman et al. |
| 5,800,393 A | 9/1998 | Sahota |
| 5,800,520 A | 9/1998 | Fogarty et al. |
| 5,814,016 A | 9/1998 | Valley et al. |
| 5,814,064 A | 9/1998 | Daniel et al. |
| 5,830,222 A | 11/1998 | Makower et al. |
| 5,830,224 A | 11/1998 | Cohn et al. |
| 5,833,644 A | 11/1998 | Zadno-Azizi et al. |
| 5,833,650 A | 11/1998 | Imran |
| 5,843,124 A | 12/1998 | Hammerslag |
| 5,843,166 A | 12/1998 | Lentz et al. |
| 5,853,409 A | 12/1998 | Swanson et al. |
| 5,855,563 A | 1/1999 | Kaplan et al. |
| 5,857,998 A | 1/1999 | Barry |
| 5,868,708 A | 2/1999 | Hart et al. |
| 5,893,867 A | 4/1999 | Bagaoisan et al. |
| 5,899,917 A | 5/1999 | Edwards et al. |
| 5,906,636 A | 5/1999 | Casscells, III et al. |
| 5,911,710 A | 6/1999 | Barry et al. |
| 5,916,264 A | 6/1999 | Von Oepen |
| 5,928,260 A | 7/1999 | Chin et al. |
| 5,928,279 A | 7/1999 | Shannon et al. |
| 5,935,075 A | 8/1999 | Cascells et al. |
| 5,938,694 A | 8/1999 | Jaraczewski et al. |
| 5,944,019 A | 8/1999 | Knudson et al. |
| 5,957,961 A | 9/1999 | Maguire et al. |
| 5,964,798 A | 10/1999 | Imran |
| 5,968,064 A | 10/1999 | Selmon et al. |
| 5,976,178 A | 11/1999 | Goldsteen et al. |
| 5,980,532 A | 11/1999 | Wang |
| 5,984,955 A | 11/1999 | Wisselink |
| 5,989,223 A | 11/1999 | Chu et al. |
| 5,997,526 A | 12/1999 | Giba et al. |
| 6,004,310 A | 12/1999 | Bardsley et al. |
| 6,013,085 A | 1/2000 | Howard |
| 6,017,365 A | 1/2000 | Von Oepen |
| 6,019,779 A | 2/2000 | Thorud et al. |
| 6,022,336 A | 2/2000 | Zadno-Azizi et al. |
| 6,022,343 A | 2/2000 | Johnson et al. |
| 6,030,406 A | 2/2000 | Davis et al. |
| 6,033,434 A | 3/2000 | Borghi |
| 6,064,902 A | 5/2000 | Haissaguerre et al. |
| 6,068,656 A | 5/2000 | Von Oepen |
| 6,071,292 A | 6/2000 | Makower et al. |
| 6,120,534 A | 9/2000 | Ruiz |
| 6,124,523 A | 9/2000 | Banas et al. |
| 6,156,064 A | 12/2000 | Chouinard |
| 6,159,197 A | 12/2000 | Heuser |
| 6,168,579 B1 | 1/2001 | Tsugita |
| 6,176,872 B1 | 1/2001 | Miksza |
| 6,187,033 B1 | 2/2001 | Schmitt et al. |
| 6,190,353 B1 * | 2/2001 | Makower et al. ........ 604/95.01 |
| 6,193,747 B1 | 2/2001 | Von Oepen |
| 6,231,587 B1 | 5/2001 | Makower |
| 6,245,052 B1 | 6/2001 | Orth et al. |
| 6,264,685 B1 | 7/2001 | Ahari |
| 6,264,690 B1 | 7/2001 | Von Oepen |
| 6,283,958 B1 | 9/2001 | Vogl et al. |
| 6,325,826 B1 | 12/2001 | Vardi et al. |
| 6,364,900 B1 | 4/2002 | Heuser |
| 6,383,214 B1 | 5/2002 | Banas et al. |
| 6,464,665 B1 | 10/2002 | Heuser |
| 6,464,684 B1 | 10/2002 | Galdonik |
| 6,475,226 B1 | 11/2002 | Belef et al. |
| 6,536,949 B1 | 3/2003 | Heuser |

| | | | |
|---|---|---|---|
| 6,582,394 | B1 | 6/2003 | Reiss et al. |
| 6,613,078 | B1 | 9/2003 | Barone |
| 6,709,455 | B1 | 3/2004 | Chouinard |
| 6,726,677 | B1 | 4/2004 | Flaherty et al. |
| 6,746,479 | B2 | 6/2004 | Ehr et al. |
| 6,858,038 | B2 | 2/2005 | Heuser |
| 6,863,684 | B2 | 3/2005 | Kim et al. |
| 6,866,805 | B2 | 3/2005 | Hong et al. |
| 6,929,009 | B2 | 8/2005 | Makower et al. |
| 6,987,660 | B2 | 1/2006 | Stevenson et al. |
| 7,056,325 | B1 | 6/2006 | Makower et al. |
| 7,059,330 | B1 | 6/2006 | Makower et al. |
| 7,094,230 | B2 | 8/2006 | Flaherty et al. |
| 7,134,438 | B2 | 11/2006 | Makower et al. |
| 7,159,592 | B1 | 1/2007 | Makower et al. |
| 7,166,088 | B2 | 1/2007 | Heuser |
| 7,179,250 | B2 | 2/2007 | Heuser |
| 7,179,270 | B2 | 2/2007 | Makower |
| 7,191,015 | B2 | 3/2007 | Lamson et al. |
| 2001/0003161 | A1 | 6/2001 | Vardi et al. |
| 2001/0049549 | A1 | 12/2001 | Boylan et al. |
| 2002/0178570 | A1 | 12/2002 | Sogard et al. |
| 2003/0055402 | A1 | 3/2003 | Zhou |
| 2003/0055484 | A1 | 3/2003 | Lau et al. |
| 2003/0139797 | A1 | 7/2003 | Johnson et al. |
| 2003/0163156 | A1 | 8/2003 | Hebert et al. |
| 2003/0199967 | A1 | 10/2003 | Hartley et al. |
| 2003/0212450 | A1 | 11/2003 | Schlick |
| 2004/0019373 | A1 | 1/2004 | Casey et al. |
| 2004/0082989 | A1 | 4/2004 | Cook et al. |
| 2004/0098095 | A1 | 5/2004 | Burnside et al. |
| 2004/0106978 | A1 | 6/2004 | Greenberg et al. |
| 2004/0116831 | A1 | 6/2004 | Vrba |
| 2004/0162603 | A1 | 8/2004 | Golds et al. |
| 2004/0167607 | A1 | 8/2004 | Frantzen |
| 2005/0125011 | A1* | 6/2005 | Spence et al. ............ 606/144 |
| 2006/0047222 | A1 | 3/2006 | Heuser |
| 2006/0217799 | A1 | 9/2006 | Mailander et al. |
| 2006/0229638 | A1 | 10/2006 | Abrams et al. |
| 2007/0021730 | A1 | 1/2007 | Flaherty et al. |
| 2007/0083257 | A1 | 4/2007 | Pal et al. |

FOREIGN PATENT DOCUMENTS

| | | |
|---|---|---|
| EP | 0707864 | 4/1996 |
| EP | 0819411 | 1/1998 |
| EP | 0917886 | 5/1999 |
| EP | 1421970 | 5/2004 |
| FR | 2753907 | 3/1998 |
| JP | 0003094773 | 4/1991 |
| WO | WO9214406 | 9/1992 |
| WO | WO9640348 | 12/1996 |
| WO | WO9717101 | 5/1997 |
| WO | WO9800090 | 1/1998 |
| WO | WO9811933 | 3/1998 |
| WO | WO9819632 | 5/1998 |
| WO | WO9826731 | 6/1998 |
| WO | WO9839047 | 9/1998 |
| WO | WO9908744 | 2/1999 |
| WO | WO9913808 | 3/1999 |
| WO | WO9924105 | 5/1999 |
| WO | WO9934749 | 7/1999 |
| WO | WO9936002 | 7/1999 |
| WO | WO0166038 | 3/2001 |
| WO | WO2005096995 | 10/2005 |

OTHER PUBLICATIONS

American Journal of Surgery: *Revascularization of Severely Ischemic Extremities with an Arteriovenous Fistula*. Aug. 1966.

Basic Research in Cardiology: *Collateral vessel formation: isolation of a transferable factor promoting a vascular respones*. Jan. 9, 1975.

Ann. Surg.: *Use of an Arteriovenous Fistula for Treatment of the Severely Ischemic Extremity: Experimental Evaluation*. Nov. 1976.

Br. J. Surg.: *Treatment of critical ischaemia of the lower limb by venous arterialization: an interim report*. 1977.

Surgery: *Acute physiologic effects of arteriovenous anastomosis and fistula in revascularizing the ischemic canine hind limb*. Apr. 1981.

JAMA: *Lipid Angiogenic Factor from Omentum*. Oct. 19, 1984.

The Lancet: *Angiogenesis Factor from Human Myocardial Infarcts*. Aug. 13, 1983.

Surgery, Gynecology & Obstetrics: *An Angiographic Study of Ischemia as a Determinant of Neovascularization in Arteriovenous Reversal*. Jan. 1988.

Blaisdell, M.D., William, et al. "Revascularization of Severely Ischemic Exrtremeties with an Arteriovenous Fistula." American Journal of Surgery. Aug. 1966. pp. 166-174. vol. 112.

Elsner, M.D., Mathias, et al. "Coronary Stent Grafts Covered by a Polytetrafluoroethylene Membrane." The American Journal of Cardiology. Aug. 1, 1999. pp. 335-338. vol. 84.

English Abstract of JP0003094773 of Inaba et al.

Halstead, M.D., Albert. "Arteriovenous Anastomosis in the Treatment of Gangrene in the Extremities." Surgery, Gynecology and Obstetrics. 1912. pp. 1-19. vol. 16.

Heuser, M.D., Richard R., et al. "Endoluminal Grafting for Percutaneous Aneurysm Exclusion in an Aortocoronary Saphenous Vein Graft: The First Clinical Experience." Journal of Endovascular Surgery. 1995. pp. 81-88. vol. 2.

Howell, M.D., Marcus, et al. "Preliminary Results of Endovascular Abdominal Aortic Aneurysm Exclusion with the AneuRx Stent-Graft." Journal of the American College of Cardiology. 2001. pp. 1040-1048. vol. 38, No. 4.

Johnson & Johnson Gateway, LLC. "Chronic Total Occlusion (CTO) Technologies." http://www.jnjgateway.com/home.jhtml?loc=USENG&page=viewContent&contentId=09008b9881163810&parentId=09008b9881163810. 2007. Printed Jan. 17, 2007.

Kalmar, M.D., Gabor, et al. "Radial Force and Wall Apposition of Balloon-expandable Vascular Stents in Eccentric Stenoses: An In Vitro Evaluation in a Curved Vessel Model." Journal of Vascular and Interventional Radiology. May 2002. pp. 499-508. vol. 13, No. 5.

Oesterle, et al., "An Embolization Containment Device." Catheterization and Cardiovascular Interventions. 1999. pp. 243-250. vol. 47.

Robertson, M.D., Roy, et al. "Collateral Circulation in the Presence of Experimental Arteriovenous Fistula." Surgery. Jan. 1950. pp. 1-16. vol. 27, No. 1.

Rossi, Anne V. "510(k) Summary per 21 CFR 807.92 re BSC IQ Hydrophilic Guide Wire and Response Letter from Department of Health and Human Services." Aug. 1, 2003.

Terumo Medical Corporation. "Glidewire Hydrophilic Coated Guidewire Designed for Peripheral Applications." http://www.terumomedical.com/SubDepts.asp?myID=79. 2002. Printed Jan. 30, 2007.

Heuser, M.D., Richard R., et al. "The Use of a New Wire in a 6-Year-Old Coronary Artery Occlusion: The Jagwire Recanalization Guidewire." Catheterization and Cardiovascular Diagnosis. 1993. pp. 173-176, vol. 29.

* cited by examiner

CATHETER SYSTEM FOR CONNECTING ADJACENT BLOOD VESSELS

BACKGROUND

This invention relates generally to a catheter system for connecting adjacent blood vessels, e.g., an artery and an adjacent vein to adapt the vein for arterial blood flow. More particularly the invention concerns a system of two catheters with mating, magnetic tips for creating openings in the artery wall and vein wall to form a fistula connecting the blood vessels.

A catheter apparatus and method for arterializing a section of a vein to bypass a clogged artery are shown in U.S. Pat. No. 6,464,665, which is hereby incorporated by reference. The method is used to bypass a stenosis in the artery that obstructs blood flow in a portion of the artery. If the obstructed portion of the artery can be bypassed, blood flow will be restored downstream from the stenosis. A vein running alongside the artery in the obstructed portion of the artery can be used for the bypass.

The catheter apparatus includes one catheter for inserting into the artery and another catheter for inserting into the adjacent vein. The physician maneuvers the tips of both catheters to coincident positions within each blood vessel adjacent one end of the obstructed portion of the artery. The physician then creates an opening from the inside of one blood vessel through the vessel wall and then through the wall of the other blood vessel. A difficulty here is in co-locating the openings in the two blood vessels and holding the vessel walls in place to ensure that a channel will be created between the vessels so that blood will flow from one vessel to the other.

SUMMARY OF THE INVENTION

The invented system and method provides for creating paired, co-located openings and a consequent fistula between an artery and an adjacent vein to bypass an arterial blockage. The system includes a piercing tool on a first catheter that mates with a receptor on a second catheter to create the co-located openings at one side of the blockage. Magnets incorporated in either or both catheters may be used to draw the piercing tool into the receptor. The piercing tool and receptor typically are provided with complementary, mating contours to draw the piercing tool sufficiently into the receptor to ensure completion of the openings. The openings may be expanded by balloon angioplasty and a stent is typically then installed to interconnect the openings to ensure a fistula is established between the vessels. The process may be repeated at the other side of the arterial blockage to complete the bypass.

DETAILED DESCRIPTION OF THE PREFERRED EMBODIMENTS

Figure 1:
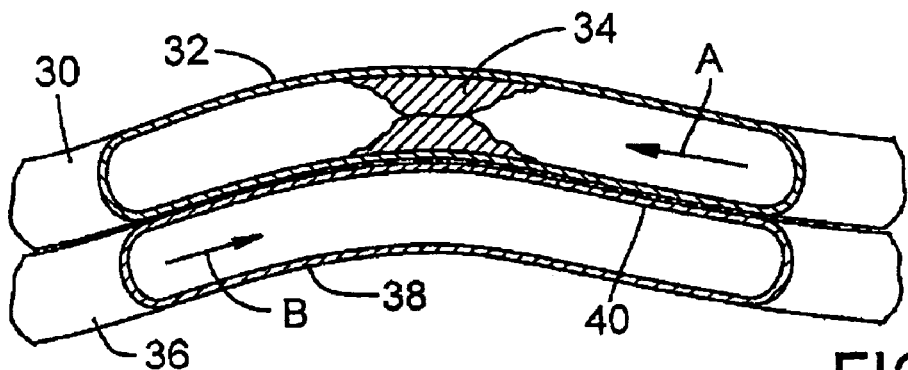
FIG. 1 is a partial cross-sectional view showing an obstructed artery, including the obstruction and the area adjacent both ends of the obstruction, and a vein alongside the artery.

As shown in FIG. 1, an artery 30, formed by an artery wall 32, has a blood flow, indicated by arrow A, that is partially or totally blocked by an obstruction or occlusion 34, typically formed by plaque. A vein 36 roughly similar in dimension to artery 30 lies alongside and generally parallel to artery 30. Vein 36, formed by a vein wall 38, includes, in the area proximal to occlusion 34, a portion 40 in close proximity to artery 30 that the physician has selected as a venous site for creating a fistula between artery 30 and vein 36. The normal blood flow through vein 36 would be in the direction indicated by arrow B.

Figure 2:
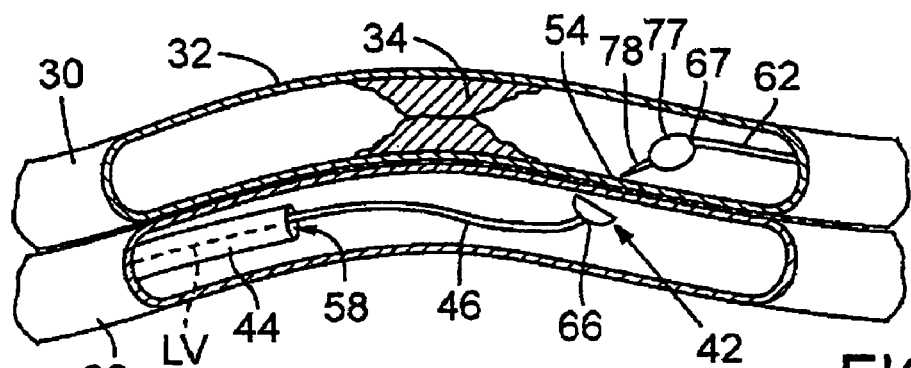
FIG. 2 is a cross-sectional view of an embodiment of the present invention in the blood vessels of FIG. 1 with a first catheter with a distal end inserted into the artery and a second catheter with a distal end inserted into the vein, the catheters carrying at their distal ends mating tips, i.e., a piercing tool on the first catheter and a receptor on the second catheter.

An embodiment of the invented system, indicated generally at 42 in FIG. 2, is a catheter apparatus that includes a first catheter 62 and a second catheter 44. In FIG. 2, the first catheter is in the artery and the second catheter is in the vein, but this can be reversed. Similarly, the first catheter in the artery is shown upstream from occlusion 34, but this may alternatively be reversed to begin the procedure downstream from the occlusion and proceeding afterwards to the upstream side.

Second catheter 44 may include at least one lumen 58 which runs generally parallel to a longitudinal axis LV of catheter 44. A wire 46 may be inserted through lumen 58.

Typically, wire 46 has an outer diameter of 0.035-inches, but any suitable dimension may be used. Wire 46 may be controllable by the physician in position relative to catheter 44. Wire 46 may be a guidewire for catheter 44, or a separate guidewire may be used, with other lumens in catheter 44 providing the channel for the separate guidewire.

As shown in FIG. 2, first catheter 62 of catheter apparatus 42 includes a distal end 67 that the physician may insert into artery 30 for positioning adjacent arterial fistula site 54. First catheter 62 may include one or more lumens running generally parallel to a longitudinal axis of catheter 62. First catheter 62 may be guided along a guidewire or may itself be a guidewire, typically with an outer diameter of 0.035-inches, although any suitable dimension may be used. First catheter 62 preferably is hollow.

Figure 3:
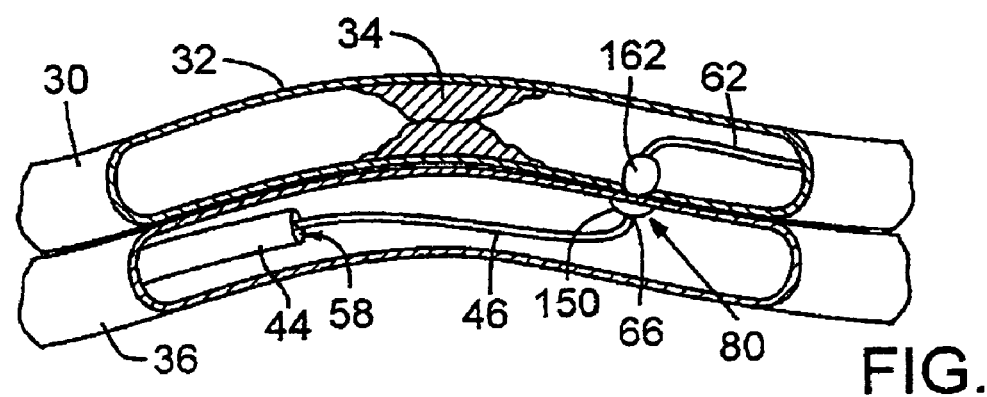
FIG. 3 is a cross-sectional view of the vein, artery, and two catheters, as in FIG. 2 with the tips of the catheters mated to create a pair of co-located openings in the walls of the vein and artery for connection of a fistula between the artery and the vein.

A piercing tool 77 that includes a sharp needle 78, may be selectively deployed, as shown in FIGS. 2 and 3, or withdrawn into the lumen of catheter 62. Needle 78 is preferably withdrawn while catheter 44 is maneuvered to the fistula site so as not to cause trauma to the blood vessel wall.

Figure 9:
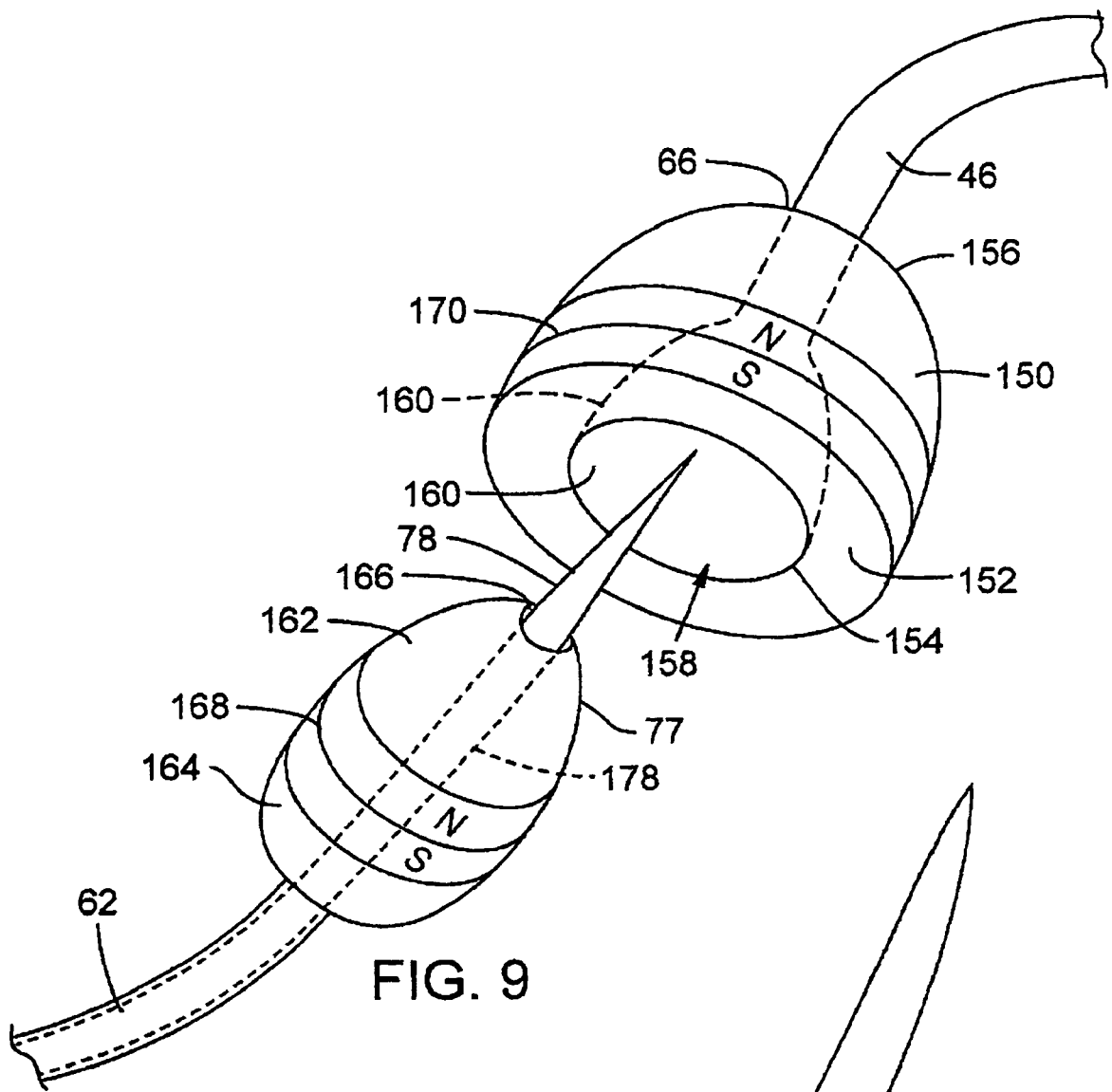
FIG. 9 is a close-up perspective view of the mating tips of the first and second catheters, showing the receptor, which includes a proximal end, a distal opening, and a channel providing a guide surface, and the piercing tool, which includes a needle and a plug encompassing the catheter adjacent the base of the needle, and showing the contours of the plug, needle, and receptor channel that provide for mating between the tips.

As best seen in FIG. 9, needle 78 may be disposed at the distal end of a wire 178 disposed in the lumen of catheter 62. The physician can control the positioning of wire 178 and needle 78 relative to catheter 62. Guidewire 46 may include a receptor 150, such as substantially cup-shaped socket 152. Receptor 150 includes a distal opening 154, preferably circular, and a proximal end 156. Receptor 150 includes a channel 158 leading from opening 154 toward proximal end 156. Channel 158 preferably narrows in a direction from opening 154 toward proximal end 156. Channel 158 is defined by an inner surface 160 that provides a guide surface for needle 78 that directs the needle toward proximal end 156 of receptor 150. Channel 158 may be substantially conical, or have such other shape as tends to mate with, and guide piercing tool 77 into receptor 150.

Piercing tool 77 on catheter 62 preferably includes a plug 162 provided with an outer contour that narrows from a proximal end 164 toward a distal end 166. Plug 162 preferably mates with channel 158 in receptor 150. Plug 162 preferably encompasses catheter 62 adjacent the distal end of the catheter. As seen in FIGS. 2, 3, and 9, the piercing tool and the receptor have a complementary configuration that supports their mating together.

Typically, piercing tool 77 will include a magnet with one pole oriented toward the distal end of the tool, while receptor 150 will include a magnet with the opposite pole oriented toward the distal end of the receptor which will draw the needle into the receptor. For example, the magnets may be annular rings or donuts and formed of a strong permanent magnet material suitable for the intended use.

A typical arrangement, shown in FIG. 9, is that plug 162 includes a first magnet 168 generally in a donut shape and having a north pole N positioned distally with respect to a south pole S. Typically magnet 168 is spaced from the distal end of plug 162. A second magnet 170 may be disposed on, or form an integral part of receptor 152, preferably adjacent distal opening 154 of socket 152. Second magnet 170 may be arranged with a south pole S distal of a north pole N to attract magnet 168 when the tips of the two catheters are in proximity, e.g., with each catheter in an adjacent blood vessel. Alternatively or in addition one or more magnets may be arranged in various locations on plug 162 and/or needle 78 and on or in receptor 150, e.g., adjacent proximal end 156, with the poles arranged to draw piercing tool 77 into receptor 150.

Figure 4:
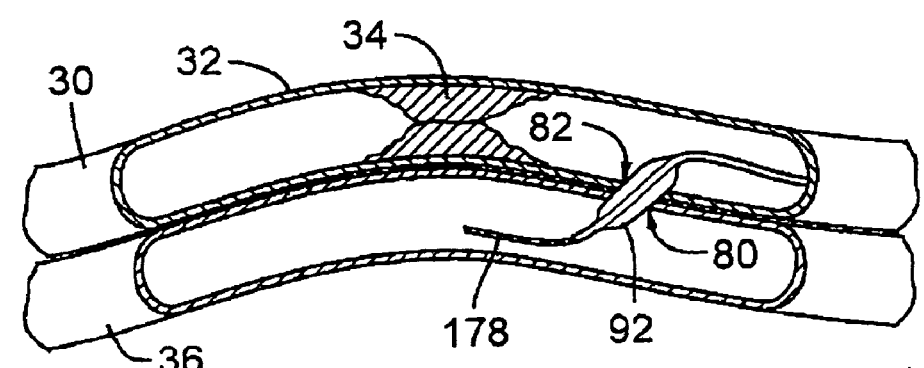
FIG. 4 is a cross-sectional view of the vein and artery with a balloon inserted through both openings.

As shown in FIGS. 3 and 4, after creating openings 80, 82 with a tool such as needle 78, the physician withdraws catheter 62 from the fistula site, leaving wire 178 in place, and a balloon 92 may be inserted over wire 178 and through openings 80, 82 and inflated to enlarge the openings. Balloon 92 may include radiopaque markers and may be inflated with a solution containing a radiopaque dye or contrast to allow the physician to radiographically monitor and adjust the position of the balloon before, during, and after inflation.

Figure 5:
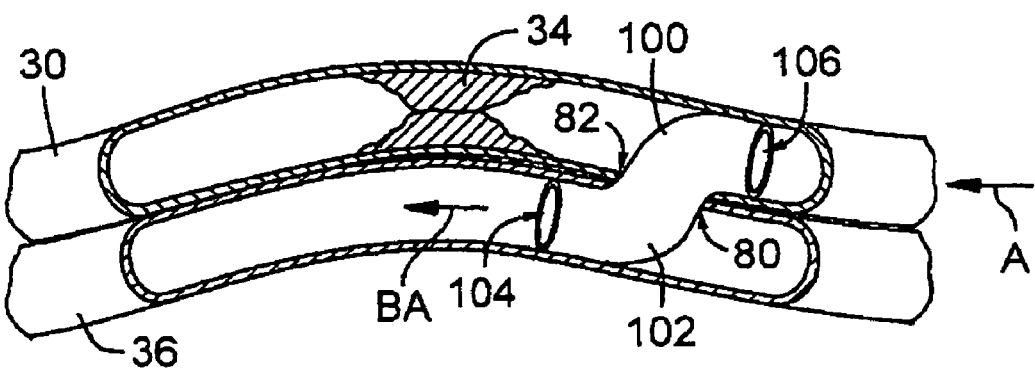
FIG. 5 is a cross-sectional view of the vein and artery with a stent installed through the openings between the vein and artery to maintain a fistula therebetween.

As shown in FIG. 5, a device for maintaining an open, leak-free connection between openings 80 and 82, such as stent 100, is inserted through the openings. Stent 100 includes a frame 102 having two open ends 104 and 106 that preferably create leak-free couplings to the inside of artery 30 and vein 36. With openings 80, 82 connected to form a fistula, vein 36 is arterialized, and blood flows from artery 30 into vein 36 in the direction indicated by arrows A and BA.

Stent 100 is typically a short, covered stent, such as the Hemobahn stent made by WL Gore & Associates.

Figure 6:
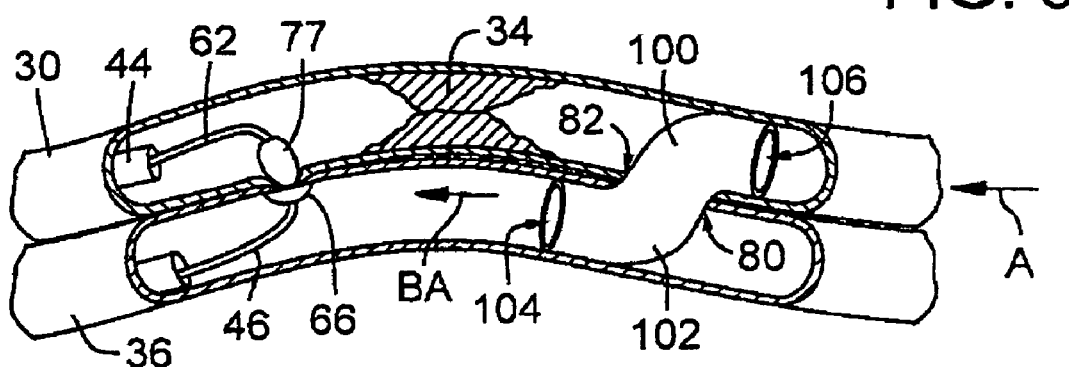
FIG. 6 is a cross-sectional view of a first catheter inserted in the artery and a second catheter inserted in the vein at the other end of the obstruction depicted in FIGS. 1-4, the catheters including mating tips shown in a joined position to create a second pair of co-located openings through the vein and artery walls.
Figure 7:
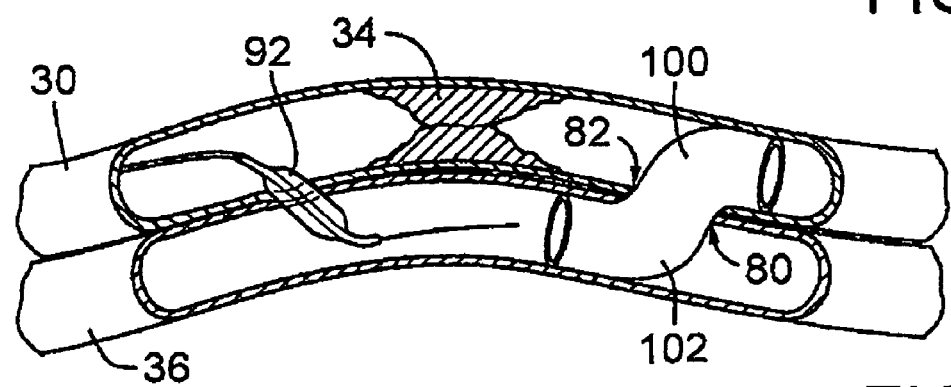
FIG. 7 is a cross-sectional view of the vein and artery with a balloon inserted through the second pair of openings between the vein and the artery.
Figure 8:
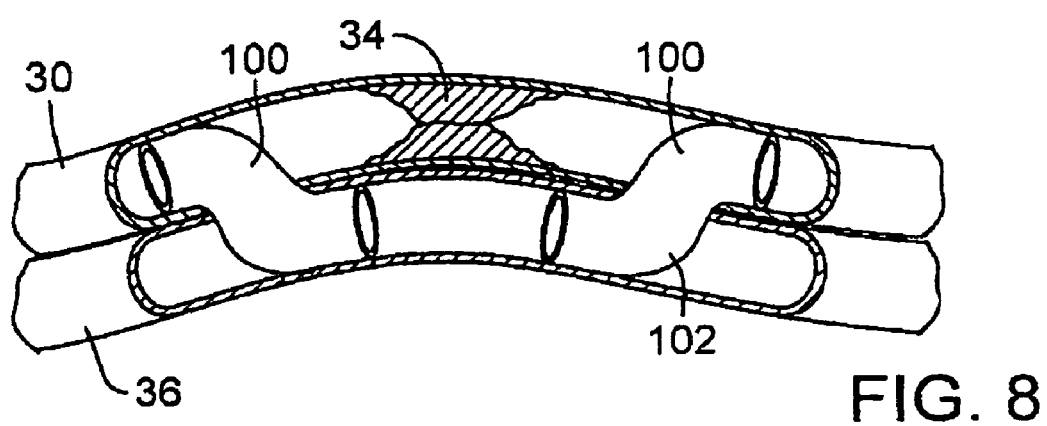
FIG. 8 is a cross-sectional view of the vein and artery with a second stent installed through the second pair of openings between the vein and artery to maintain a fistula therebetween.

As shown in FIGS. 6, 7, and 8 a second pair of co-located openings may be created, and a stented fistula established therebetween, using essentially the same catheter system and method as described for FIGS. 1-5 and 9. FIG. 6 illustrates that the first catheter with the piercing tool preferably is inserted into the artery and the openings created from the artery into the vein. Alternatively the openings may be created from the vein into the artery.

Figure 10:
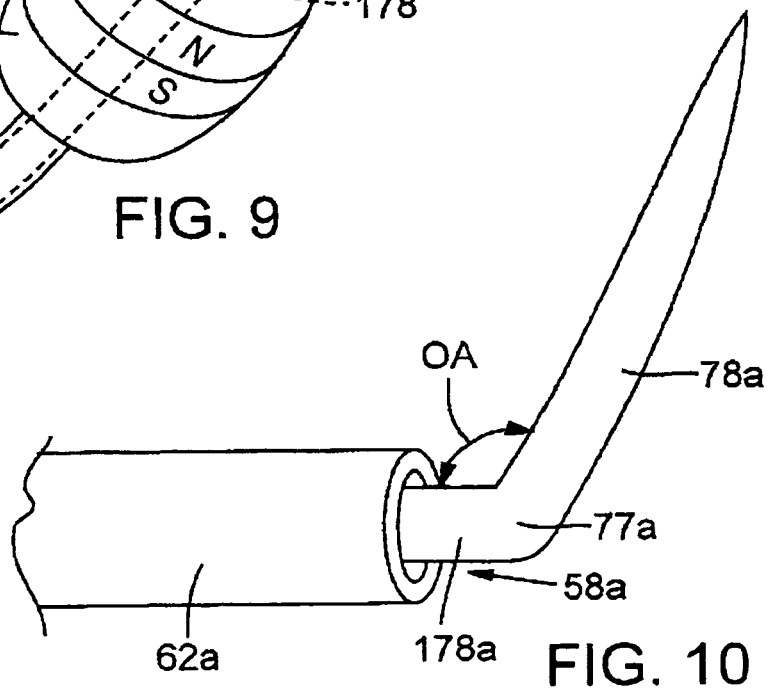
FIG. 10 is a piercing tool for use in a second embodiment of the present invention that includes a base and a needle that is offset from the base by an angle.

An alternative embodiment for the piercing tool in shown in FIG. 10. This tool 77a may be used with a metal guidewire 62a that preferably includes a lumen 58a. An inner wire 178a may be inserted in lumen 58a, providing a base for a needle 78a. The coupling between the needle and base incorporates a curvature such that the needle is nominally offset from the base by an angle OA, typically between about 30-degrees and about 90-degrees. Inner wire 178a is typically made of a sufficiently rigid material, such as nitinol and/or stainless steel, as to maintain the offset angle as the needle is used to pierce blood vessels. Guidewire 62a is preferably formed of a sufficiently rigid material such that when needle 78a is retracted into lumen 58a, the curvature between the needle and the base is overcome and the needle temporarily aligns with the base in a non-traumatic configuration. Inner wire 178a may have an outer diameter of 0.010, 0.014, 0.018, or 0.021-inches, or such other dimension as is suited to the particular application.

Figure 11:
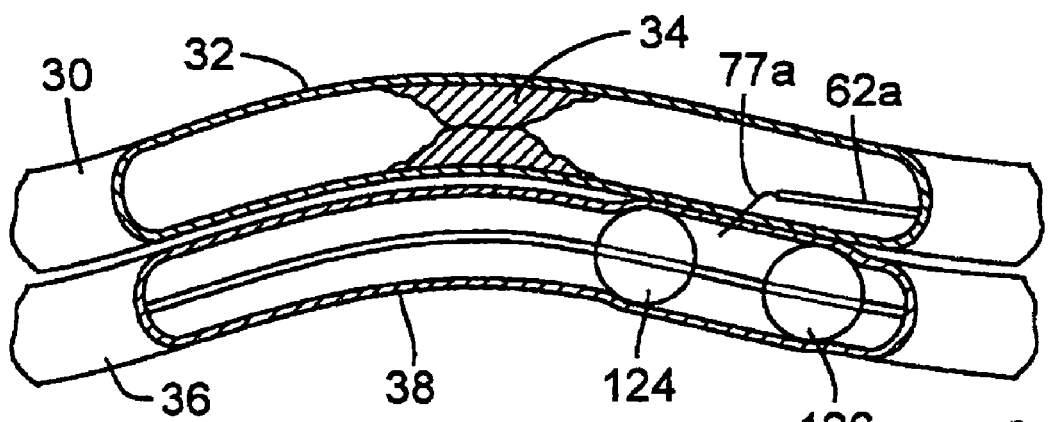
FIG. 11 illustrates the use of the piercing tool of FIG. 10 in conjunction with a double-balloon catheter to create openings in a vein and an artery.

As shown in FIG. 11, piercing tool 77a may be inserted in artery 30, typically while withdrawn into the catheter 62a while maneuvering to the fistula site. Piercing tool 77a may be used in conjunction with a catheter having two balloons 124 and 126 that are inserted in vein 36. In such case, the catheter tips are maneuvered to opposing sides of the proposed fistula site and balloons 124 and 126 are inflated to press the vein wall against the artery wall. Also, fluid may be injected into the sealed-off area to further press the two blood vessel walls together. Then piercing tool 77a is deployed and maneuvered through the artery and then the vein wall to create openings for forming the fistula as for the embodiments described above.

FIG. 11 depicts the piercing tool and the balloon catheter in different vessels. Alternatively, piercing tool 77a may be inserted in the same blood vessel with the balloon catheter. In such an embodiment, the balloons are preferably independently inflatable, and typically the distal balloon 124 is inflated first to stop blood flow. Then, piercing tool 77a is maneuvered to the fistula site in a manner similar to that for the previously described embodiment, typically with the piercing tool withdrawn into the guidewire to the non-traumatic configuration.

With the piercing tool at the fistula site, the proximal balloon 126 is inflated to seal off the fistula site and also to press the vein against the artery. Then, piercing tool 77a is deployed at the end of guidewire 62a and maneuvered by the physician to create the openings from one blood vessel, through both walls, to the other blood vessel.

In either case, piercing tool 77a may be used to create multiple pairs of co-located openings which are then stented to arterialize a portion of the vein to bypass a blockage using a similar method as described above for the embodiment of FIGS. 1-9.

Figure 12:
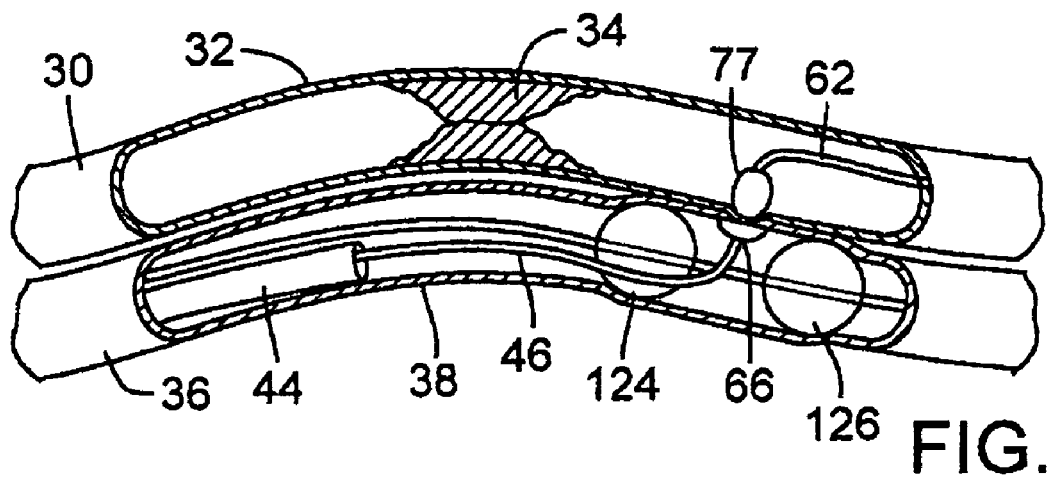
FIG. 12 illustrates the use of the piercing tool of FIGS. 2, 3, 6, and 9 in conjunction with a double-balloon catheter to create openings in a vein and an artery.

As shown in FIG. 12, the double balloon catheter may also be used in conjunction with the catheters 44 and 62 that include the mating tips. In this embodiment, the double balloon catheter helps to control blood flow at the planned fistula site and to press the blood vessel walls together to assist in the mating of the tips. The fistula creation otherwise proceeds in a similar manner as for the embodiment of FIGS. 1-9.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also included within the subject matter of the inventions of the present disclosure.

I claim:

1. A catheter system for piercing a first wall of a first blood vessel and a second wall of a second blood vessel to create a fistula between the blood vessels, the system comprising:
   a first catheter having a distal end insertable to a position wherein the distal end is adjacent a site within the first blood vessel for the fistula, the first catheter including a magnetic piercing tool adjacent the distal end;
   a second catheter having a distal end insertable to a position wherein the distal end is adjacent a site within the second blood vessel for the fistula, the second catheter including adjacent the distal end a receptor having a distal opening and a proximal end, the receptor further including a channel leading from the opening toward the proximal end wherein the entire channel of the receptor narrows in a direction from the opening toward the proximal end, and
   one or more magnets disposed on at least one of the catheters to draw the piercing tool into the channel of the receptor.

2. The catheter system of claim 1 wherein the channel is substantially conical.

3. The catheter system of claim 1 wherein one magnet is disposed at the proximal end of the receptor.

4. The catheter system of claim 1 wherein one magnet is disposed on the first catheter proximally with respect to the piercing tool.

5. The catheter system of claim 4 wherein the magnet on the first catheter encompasses the catheter adjacent the distal end and includes a portion that fits into the channel of the receptor.

6. The catheter system of claim 1 wherein the piercing tool and the receptor are provided with a complementary configuration.

7. The catheter system of claim 1 further including a third catheter having a double balloon disposed adjacent a distal end thereof, the double balloon maneuverable in either blood vessel to the fistula site.

8. A catheter system for piercing a first wall of a first blood vessel and a second wall of a second blood vessel to create a fistula between the blood vessels, the system comprising:
   a first catheter having a distal end insertable to a position wherein the distal end is adjacent a site within the first blood vessel for the fistula, the first catheter including a magnetic piercing tool adjacent the distal end;
   a second catheter having a distal end insertable to a position wherein the distal end is adjacent a site within the second blood vessel for the fistula, the second catheter including adjacent the distal end a receptor configured to receive the piercing tool and having a distal opening, a proximal end, and a guide surface disposed between the distal opening and the proximal end, wherein the guide surface of the receptor directs the piercing tool toward the proximal end and the entire guide surface narrows in a direction from the distal opening towards the proximal end, and
   one or more magnets disposed on at least one of the catheters to draw the piercing tool along the guide surface of the receptor.

9. The catheter system of claim 8 wherein the guide surface includes a conical section.

10. The catheter system of claim 8 wherein one magnet is disposed at the proximal end of the receptor.

11. The catheter system of claim 8 wherein one magnet is disposed on the first catheter proximally with respect to the piercing tool.

12. The catheter system of claim 11 wherein the magnet on the first catheter encompasses the catheter adjacent the distal end and includes a portion that mates with the guide surface of the receptor.

13. The catheter system of claim 8 wherein the piercing tool and the receptor are provided with a complementary configuration.

14. The catheter system of claim 8 further including a third catheter having a double balloon disposed adjacent a distal end thereof, the double balloon maneuverable in either blood vessel to the fistula site.

15. A catheter system for piercing a first wall of a first blood vessel and a second wall of a second blood vessel to create a fistula between the blood vessels, the system comprising:
   a first catheter having a distal end insertable to a position wherein the distal end is adjacent a site within the first blood vessel for the fistula, the first catheter including a magnetic piercing tool adjacent the distal end, the first catheter further including an outer contour that narrows toward the distal end of the first catheter;

a second catheter having a distal end insertable to a position wherein the distal end is adjacent a site within the second blood vessel fro the fistula, the second catheter including adjacent the distal end a receptor having a distal opening and a proximal end, the receptor further including a channel, defined by an inner surface, leading from the opening toward the proximal end, and one or more magnets disposed on at least one of the catheters to draw the piercing tool into the channel of the receptor so that the outer contour compliments the inner surface.

16. The catheter system of claim 15 wherein the channel is substantially conical.

17. The catheter system of claim 15 wherein one magnet is disposed at the proximal end of the receptor.

18. The catheter system of claim 15 wherein one magnet is disposed on the first catheter proximally with respect to the piercing tool.

19. The catheter system of claim 18 wherein the magnet on the first catheter encompasses the catheter adjacent the distal end and includes a portion that fits into the channel of the receptor.

20. The catheter system of claim 15 wherein the piercing tool and the receptor are provided with complimentary configuration.

21. The catheter system of claim 15 further including a third catheter having a double balloon disposed adjacent a distal end thereof, the double balloon maneuvaerable in either blood vessel to the fistula site.

* * * * *